(12) United States Patent
Fosaaen

(10) Patent No.: US 8,959,987 B2
(45) Date of Patent: Feb. 24, 2015

(54) OXYGEN SENSING METHOD AND APPARATUS

(71) Applicant: Kerdea Technologies, Inc., Greenville, NC (US)

(72) Inventor: Ken Ervin Fosaaen, Winterville, NC (US)

(73) Assignee: Kerdea Technologies, Inc., Greenville, NC (US)

( * ) Notice: Subject to any disclaimer, the term of this patent is extended or adjusted under 35 U.S.C. 154(b) by 0 days.

(21) Appl. No.: 14/073,209

(22) Filed: Nov. 6, 2013

(65) Prior Publication Data

US 2014/0130588 A1    May 15, 2014

Related U.S. Application Data

(60) Provisional application No. 61/725,209, filed on Nov. 12, 2012.

(51) Int. Cl.
*F02D 41/14* (2006.01)
*G01M 15/10* (2006.01)
*F02D 41/24* (2006.01)
*G01N 27/406* (2006.01)

(52) U.S. Cl.
CPC .......... *G01M 15/104* (2013.01); *F02D 41/1445* (2013.01); *F02D 41/1455* (2013.01); *F02D 41/1458* (2013.01); *F02D 41/2416* (2013.01); *F02D 41/2438* (2013.01); *F01N 2560/025* (2013.01); *F02D 41/1446* (2013.01); *G01N 27/4065* (2013.01)
USPC .................................... 73/114.72; 73/114.73

(58) Field of Classification Search
USPC ......................................... 73/114.72, 114.73
See application file for complete search history.

(56) References Cited

U.S. PATENT DOCUMENTS

| | | |
|---|---|---|
| 3,915,135 A | 10/1975 | Kushida et al. |
| 4,245,314 A | 1/1981 | Henrich et al. |
| 4,263,652 A | 4/1981 | Henrich |
| 4,276,600 A | 6/1981 | Hartford et al. |
| 4,462,890 A | 7/1984 | Touda et al. |
| 4,463,594 A | 8/1984 | Raff et al. |
| 4,500,412 A | 2/1985 | Takahashi et al. |
| 4,535,316 A | 8/1985 | Wertheimer et al. |

(Continued)

FOREIGN PATENT DOCUMENTS

| | | |
|---|---|---|
| CN | 101825032 A | 9/2010 |
| EP | 0488791 A2 | 6/1992 |

(Continued)

*Primary Examiner* — Freddie Kirkland, III
(74) *Attorney, Agent, or Firm* — Coats & Bennett, PLLC

(57) ABSTRACT

A method of determining an air:fuel ratio of a combustion process based on information from an oxygen sensor exposed to exhaust gases of the combustion process. A first value is determined indicative of the exhaust gas oxygen content, with the value being based on a resistance of an oxygen sensing portion of the oxygen sensor. A second value is determined indicative of a temperature of the oxygen sensor, which may be based on a resistance of a heater portion of the oxygen sensor. A third value is determined indicative of the air:fuel ratio as a function of the first and second values. Thus, the oxygen level data from the oxygen sensor may be temperature compensated so as to result in a more accurate estimate of the air:fuel ratio. The third value may then be used to control the combustion process, which may be associated with an internal combustion engine.

20 Claims, 7 Drawing Sheets

(56) References Cited

U.S. PATENT DOCUMENTS

| | | | |
|---|---|---|---|
| 4,660,407 A | 4/1987 | Takami | |
| 4,744,344 A | 5/1988 | Morozumi | |
| 5,249,453 A * | 10/1993 | Usami et al. | 73/23.32 |
| 5,322,047 A | 6/1994 | Oliu et al. | |
| 5,895,591 A | 4/1999 | Kojima | |
| 6,227,033 B1 | 5/2001 | Kainz | |
| 6,256,981 B1 | 7/2001 | Sullivan et al. | |
| 6,382,015 B1 * | 5/2002 | Aoki | 73/23.32 |
| 6,746,584 B1 | 6/2004 | Wang et al. | |
| 6,918,385 B2 * | 7/2005 | Ohkuma et al. | 123/694 |
| 7,236,083 B2 * | 6/2007 | Izu et al. | 338/34 |
| 7,769,534 B1 | 8/2010 | Xu et al. | |
| 7,846,313 B2 * | 12/2010 | Tashiro et al. | 204/406 |
| 7,954,365 B2 | 6/2011 | White et al. | |
| 8,086,392 B2 | 12/2011 | Anilovich et al. | |
| 2001/0000956 A1 * | 5/2001 | Honda et al. | 338/34 |
| 2003/0089358 A1 | 5/2003 | Ohkuma et al. | |
| 2004/0060550 A1 | 4/2004 | Wu et al. | |
| 2005/0236271 A1 * | 10/2005 | Izu et al. | 204/424 |
| 2008/0109148 A1 * | 5/2008 | Tashiro et al. | 701/109 |
| 2009/0173326 A1 * | 7/2009 | Aoki | 123/693 |
| 2011/0186446 A1 | 8/2011 | Fosaaen | |
| 2012/0102917 A1 * | 5/2012 | Gibson et al. | 60/273 |
| 2014/0130779 A1 * | 5/2014 | Fosaaen | 123/478 |
| 2014/0136082 A1 * | 5/2014 | Fosaaen | 701/109 |

FOREIGN PATENT DOCUMENTS

| | | |
|---|---|---|
| JP | 0743342 A | 2/1995 |
| JP | 4171803 B2 | 10/2008 |
| JP | 4607163 B2 | 1/2011 |
| WO | 2011093975 A3 | 8/2011 |

* cited by examiner

OXYGEN SENSING METHOD AND APPARATUS

This application claims benefit of U.S. Provisional Application No. 61/725,209, filed 12 Nov. 2012, the disclosure of which is incorporated by reference herein in its entirety.

BACKGROUND

This application is related to oxygen sensors, methods of using oxygen sensors, and related systems for use with combustion processes, for example in internal combustion engines.

As known by those of skill in the art, the air:fuel ratio in combustion processes, particularly in internal combustion engines, is typically represented by lambda ($\lambda$), with $\lambda$ defined as is the actual air:fuel ratio divided by the air:fuel ratio at the exact stoichiometric mixture. Thus, in mathematical terms $\lambda = \text{air:fuel}_{actual}/\text{air:fuel}_{stoichometric}$. Values less than 1.0 are fuel-rich (rich), values greater than 1.0 are fuel-lean (lean). For many internal combustion engines, maximum power is achieved around $\lambda = 0.86$, and maximum fuel economy is achieved around $\lambda = 1.45$-$1.55$. As can be appreciated, engine management systems typically focus heavily on controlling $\lambda$. As such, most large internal combustion engines have oxygen sensors to sense exhaust gas oxygen levels, with the data from the oxygen sensor used by the engine management systems for various engine management functions. For smaller internal combustion engines, such as those used in motorcycles, all-terrain vehicles, recreational marine applications, and unmanned air vehicles, the size constraints of the engines presents difficulties in identifying suitable oxygen sensors.

Fortunately, small resistive-based oxygen sensors are known, see, for example, U.S. Patent Application Publication 2011/0186446. Such oxygen sensors find a particular application in engine management control for small internal combustion engines. In addition, such sensors are useful for individual cylinder control in multi-cylinder engines and hybrid engines for automotive and off-road applications.

The 2011/0186446 oxygen sensor may be considered as a switching oxygen sensor with some unique properties. Such sensors have a drastic change (orders of magnitude) in the resistance of the sensor element when transitioning across the stoichiometric boundary in air:fuel ratio of Lambda ($\lambda$)=1.00. For example, for the n-type semiconductor version of the 2011/0186446 sensor, above this crossover point (in the lean region with $\lambda > 1.00$), the sensor's resistance is very high and not significantly responsive to changes in the oxygen content in the gasses to which it is exposed; however, below this crossover point (in the rich region with $\lambda < 1.00$) the resistance is significantly lower and has a positive relationship with oxygen content. Conversely, for the p-type semiconductor version of the 2011/0186446 sensor, the resistance is very high in the rich region, but is lower and has a positive relationship with oxygen content in the lean region.

While the 2011/0186446 sensors are useful for many situations, such as those described in the 2011/0186446 publication, there remains a need for alternative oxygen sensor arrangements, and for alternative methods of oxygen sensing and controlling combustion processes based on the sensed oxygen level(s), and related systems.

SUMMARY

In one or more embodiments, the present invention provides a method of determining an air:fuel ratio of a combustion process, based on information from an oxygen sensor exposed to exhaust gas from the combustion process. The method includes determining a first value indicative of oxygen content of the exhaust gas based on information from an oxygen sensing portion of the oxygen sensor. The method further includes determining a second value indicative of a temperature of the oxygen sensor corresponding in time to the first value. The method also includes determining a third value indicative of the air:fuel ratio as a function of the first and second values, wherein the third value varies in dependence on both the first value and the second value. The method may continue with thereafter controlling operation of the combustion process based on the third value. The controlling operation of the combustion process may comprise adjusting a fuel metering rate based on the third value.

The determining the first value may comprise measuring a voltage drop of a circuit comprising the oxygen sensing portion. The determining the first value may comprise determining a resistance of the oxygen sensing portion, with the determining the resistance of the oxygen sensing portion comprising determining a voltage drop across a shunt resistor disposed in series with the oxygen sensing portion.

The oxygen sensor may have an electric resistance heater portion, and the second value may be determined based on a resistance of the heater portion. The determining the second value may comprise measuring a voltage drop of a circuit comprising the heater portion. The determining the second value may comprise determining the second value based on a temperature sensor of the oxygen sensor, but distinct from the heater portion of the oxygen sensor.

The determining the third value may comprise referencing a look-up table containing pre-determined values of corresponding to the first value and the second value. The determining the third value may comprise calculating the third value according to a formula, wherein the formula has the first and second values as independent variables. The oxygen sensing portion may comprises an n-type semiconductor or a p-type semiconductor.

The combustion process may occur in an internal combustion engine. In some embodiments, the engine is a multi-cylinder engine, and the oxygen sensor is associated with only one cylinder of the engine. In some embodiments, the engine is a multi-cylinder engine, and the oxygen sensor is associated with multiple cylinders of the engine.

In one or more embodiments, the present invention provides an oxygen sensing apparatus that comprises a) an oxygen sensor disposed so as to be exposed to exhaust gas from the combustion process; the oxygen sensor having an oxygen sensing portion; and b) one or more processing circuits operatively connected to the oxygen sensor and configured to: 1) determine a first value indicative of oxygen content of the exhaust gas based on information from the oxygen sensing portion of the oxygen sensor; 2) determine a second value indicative of a temperature of the oxygen sensor corresponding in time to the first value; 3) determine a third value indicative of the air:fuel ratio as a function of the first and second values, wherein the third value varies in dependence on both the first value and the second value.

The oxygen sensor may comprise a heater portion, and the one or more processing circuits may be configured to determine the second value based on a resistance of the heater portion. The one or more processing circuits may be configured to control the combustion process based on the third value.

The oxygen sensing apparatus may be a portion of an internal combustion engine. The combustion process may be in a combustion chamber or exhaust plenum of an internal combustion engine, and the one or more processing circuits may be configured to thereafter control operation of the engine based on the third value.

The various aspects discussed above may be used alone or in any combination. The various apparatus disclosed herein may operate according to any combination of various method disclosed herein, and vice versa. Further, the present invention is not limited to the above features and advantages. Indeed, those skilled in the art will recognize additional features and advantages upon reading the following detailed description, and upon viewing the accompanying drawings.

DETAILED DESCRIPTION

In one or more embodiments, the present application is directed to a method of determining an air:fuel ratio based on information from an oxygen sensor exposed to exhaust gases of a combustion process, and related systems. A first value is determined indicative of the exhaust gas oxygen content, with the value being based on a resistance of an oxygen sensing portion of the oxygen sensor. A second value is determined indicative of a temperature of the oxygen sensor, which may be based on a resistance of a heater portion of the oxygen sensor. A third value is determined indicative of the air:fuel ratio as a function of the first and second values. Thus, the oxygen level data from the oxygen sensor may be temperature compensated so as to result in a more accurate estimate of the air:fuel ratio.

For simplicity, the discussion below may generally be in the context of an oxygen sensor for a small displacement gasoline powered internal combustion engine, but it should be understood that the oxygen sensor(s) disclosed herein may be used in other internal combustion engine applications, such a hydrogen powered engines, other hydrocarbon powered engines, diesel engines, Homogeneous Charge Compression Ignition (HCCI) engines, and Reactivity Controlled Compression Ignition (RCCI) engines. Further, the disclosed method(s) may be used with other combustion processes, such as, for example, those found in furnaces and water heaters.

Figure 1:
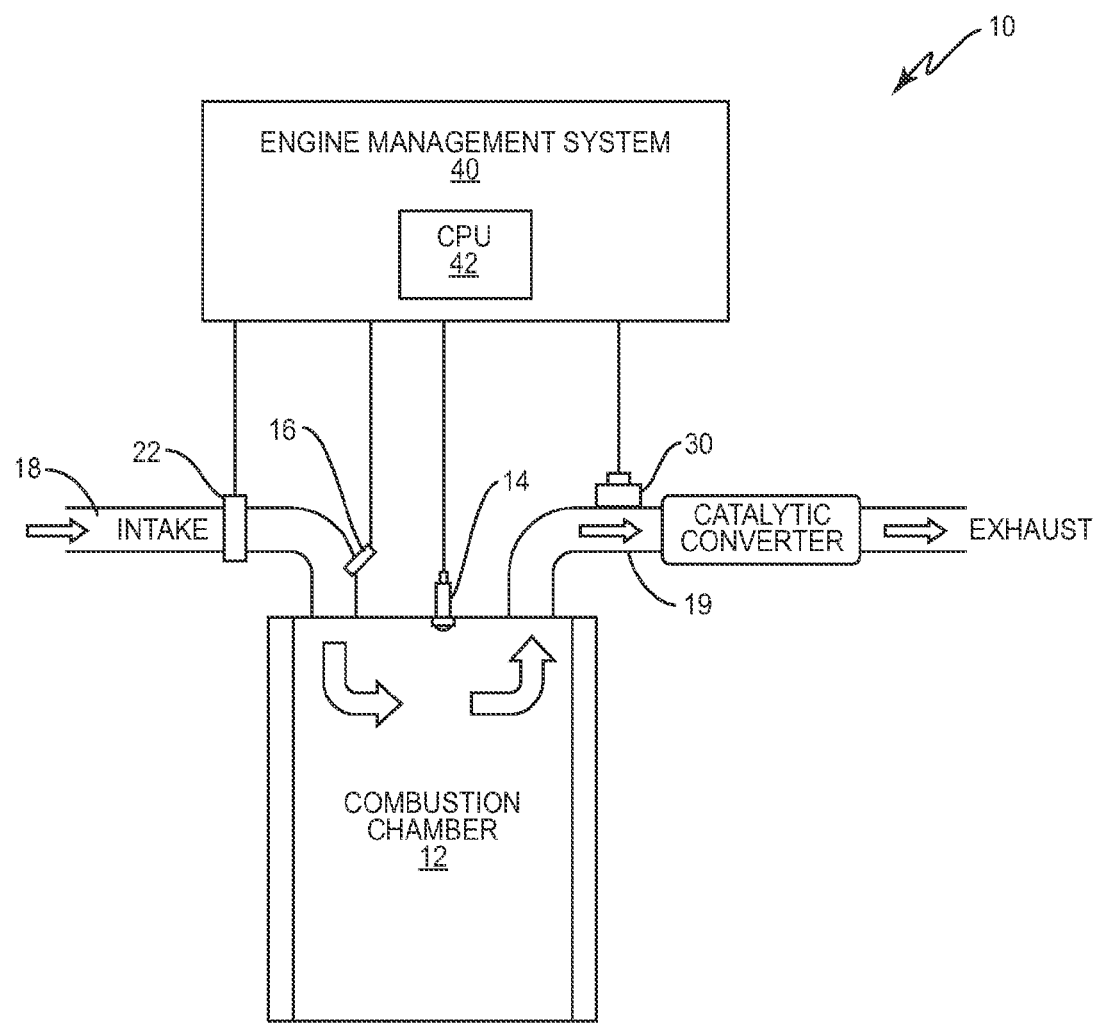
FIG. 1 shows schematic representation of an engine, where the method of the one or more embodiments of the present invention may be implemented.

FIG. 1 shows a schematic of an internal combustion engine 10, which may be of any type (e.g., piston, rotary, nutating disk, etc.). The engine 10 includes at least one combustion chamber 12 with associated piston, valves, etc. (note shown), an intake manifold 18, an exhaust manifold 19, and an engine management system 40. The intake manifold 18 supplies air to the combustion chamber 12. An mass airflow sensor 22 advantageously with associated temperature sensor is disposed in the intake 18 manifold so that the incoming air conditions may be monitored and/or controlled. A controllable fuel metering system such as a throttle body and fuel injector 16 supplies fuel to the combustion chamber under control of the engine management system 40. For spark ignition engines, a spark ignition device 14, e.g., spark plug, operates under the control of the engine management system 40 to ignite the air and fuel mixture in the combustion chamber 12 at the desired time in the cycle for proper combustion. An oxygen sensor 30 is disposed in the exhaust plenum 19 to sense the amount of oxygen in the exhaust gases, so that the proper air:fuel ratio may be properly metered and maintained. The engine management system 40 includes one or more processing circuits 42 (collectively "controller") that control the fuel supply, ignition timing, and other engine parameters based on the input from the various sensors and the programming of the processing circuits 42. For example, the engine management system 40 uses the oxygen sensor 30, as described below, to help control the engine 10 so that the engine 10 operates at the desired air:fuel ratio. Other than the particulars of the oxygen sensor 30 and the operation of the processing circuit(s) 42 described in greater detail below, the configuration and operations of the engine 10 are well known to those of skill in the art, and are not discussed further herein in the interests of clarity. As can be appreciated, the engine 10 is able to operate in a rich mode or region R where $\lambda<1.00$, in a lean mode or region L where $\lambda<1.00$, and at a stoichiometric point S where $\lambda=1.00$.

The oxygen sensor 30 is advantageously a resistive-based oxygen sensor, such as those described in U.S. Patent Application Publication No. 2011/0186446, or similar. The '6446 publication discloses, in one or more embodiments, an oxygen sensor that includes a resistance-based heater portion 34 and an n-type or p-type semiconductor that connects two intermeshing comb type electrodes for functioning as an oxygen sensing portion 32. The comb electrodes include a plurality of comb fingers having lengths and spacing. The length and spacing of the comb fingers, and the particular materials, including the semiconducting and catalytic materials, may be adjusted as desired for the particular operating conditions for the sensor 30. For purposes of the initial discussion below, the sensor 30 will be initially assumed to have an n-type semiconductor such that the resistance is significantly lower and has a positive relationship with oxygen content in the rich region R, while the resistance is relatively high and uncorrelated to the oxygen content in the lean region L.

Figure 2:
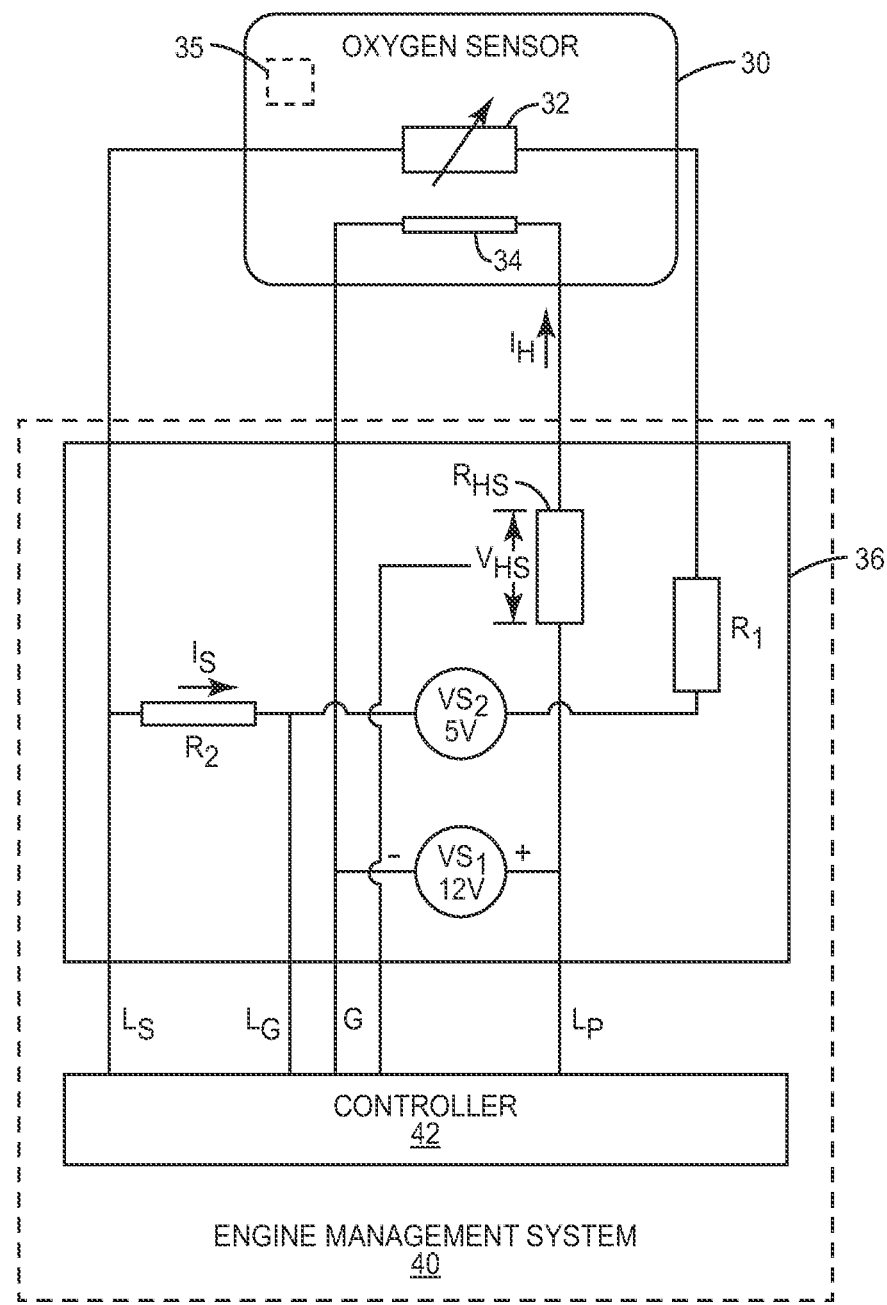
FIG. 2 shows a schematic representation of the oxygen sensor connected to the controller.
Figure 3:
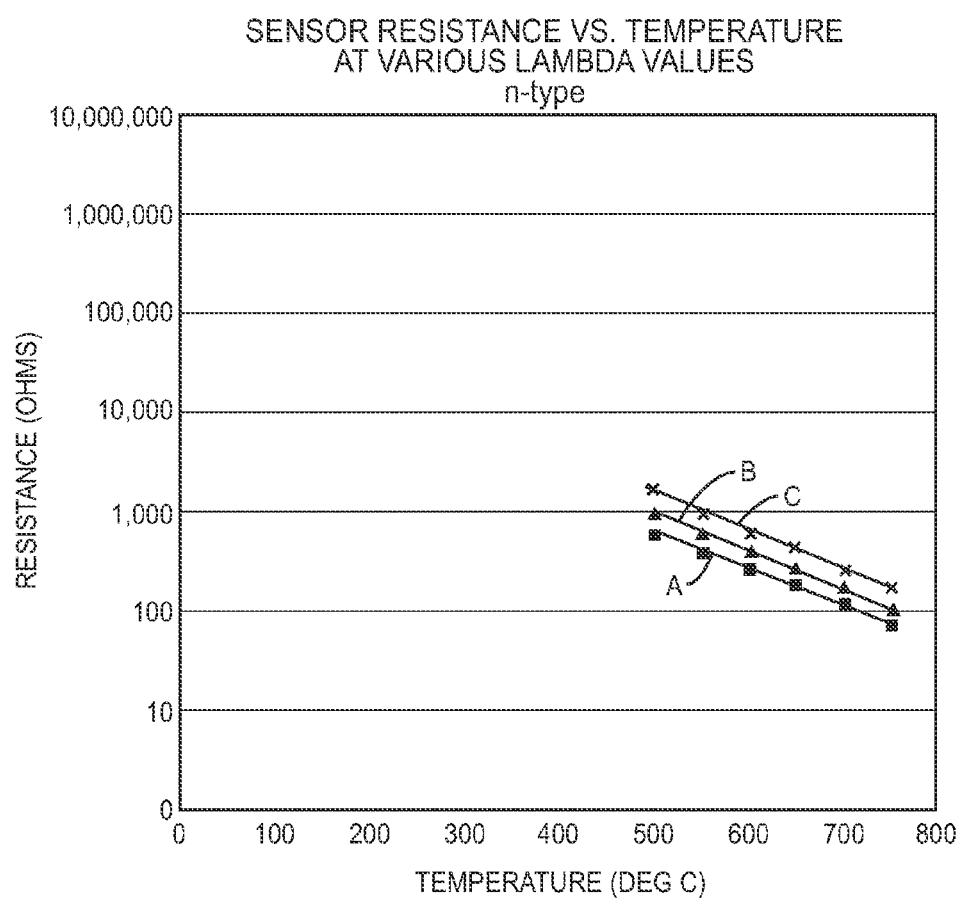
FIG. 3 shows a simplified graphic representation of temperature dependence on resistance of an n-type semiconductor based oxygen sensing circuit, at various $\lambda$ values.

Referring to FIG. 2, the oxygen sensor 30 is connected to the controller 42 so that the sensed oxygen level data from the oxygen sensing portion 32 is supplied to the controller 42. In one or more illustrative embodiments, changes in the resistance of the sensor 30 are converted into a voltage signal, such as by being routed through a resistance network 36, so that the controller 42 receives different voltage inputs for different sensed oxygen levels. The resistive network 36 may be as shown in FIG. 3, although such is not required in all embodiments. The resistor network of FIG. 3 includes a shunt resistor $R_{HS}$, resistors $R_1$ and $R_2$, a twelve volt voltage source $VS_1$, a five volt voltage source $VS_2$, a power line $L_P$, a ground line G, an oxygen sense line $L_S$, and a reference line $L_G$. The heater portion 34 is disposed between $L_P$ and G, and is supplied with power from twelve volt power source $VS_1$, via shunt resistor $R_{HS}$. A voltage drop $V_{HS}$ is measured across shunt resistor $R_{HS}$. A voltage drop $VR_2$ is measured across resistor $R_2$, between line $L_S$ and line $L_G$. The controller 42 advantageously receives $L_G$, $L_S$, and $V_{HS}$, used to calculate the relevant values as discussed further below. Note that the resistance network 36 may be integrated into an oxygen sensor assembly, integrated into the controller 42, be a separate component or components between the oxygen sensor 30 and the controller 42, or dispersed in any suitable manner. Note further that voltage drop $V_{HS}$ may be sensed via two leads, one on each side of shunt resistor $R_{HS}$, with each lead feeding a line to controller 42; this arrangement is shown in simplified fashion in FIG. 2 for clarity.

The resistance $R_S$ of the oxygen sensing portion 32 may be determined by any suitable way. For example, the current $I_S$ through the oxygen sensing portion 32 may be calculated as the voltage drop $VR_2$ across resistor $R_2$. Further, the overall resistance $R_{SC}$ along the five volt circuit through resistor $R_1$, oxygen sensing portion 32, and resistor $R_2$ may be calculated as $R_{SC}$=voltage of the circuit divided by current of the circuit, or 5 (volts) divided by $I_S$. Then, the resistance $R_S$ of the oxygen sensing portion 32 may be calculated as $R_S=R_{SC}-R_1-R_2$. Thus, the resistance $R_S$ of the oxygen sensing portion 32 may be determined based on knowledge of the voltage of voltage source $VS_2$, the resistance of resistors $R_1$ and $R_2$, the voltage drop $VR_2$ across resistor $R_2$ (voltage difference between line $L_S$ and $L_G$). In alternate embodiments, resistor $R_1$ may be omitted from the circuit, or additional resistors may be added. If resistor $R_1$ is omitted, then the resistance $R_S$ of the oxygen sensing portion 32 may be calculated as $R_S=R_{SC}-R_2$; or, if additional resistors are added, the calculation of $R_S$ advantageously takes their presence into account. The oxygen level in the exhaust gases may then be determined based on the resistance of the oxygen sensing portion 32, with the sensed oxygen level advantageously temperature compensated, as discussed further below.

The present invention takes into account that the resistance response of the oxygen sensing portion 32 is temperature dependent. For example, the resistance of oxygen sensing portion 32, with an n-type semiconductor and at a given fixed air:fuel ratio, decreases with increasing temperature, even when the temperature is clearly high enough for a good response. More particularly, at a fixed λ in the rich region (e.g., 0.85), the resistance of the oxygen sensing circuit shows what appears to be a linear decreasing relationship with increasing temperature when plotted on a log scale, as shown by curve A (lower curve) in FIG. 3. Similarly, curves B (middle curve) and C (upper curve) correspond to other λ values in the rich region (e.g., 0.90 and 0.95 respectively), and likewise appear to show a linear decreasing relationship with increasing temperature when plotted on a log scale. Thus, a relationship may be derived that relates a given combination of sensed resistance of the sensing circuit and the sensed temperature to a particular λ value. This relationship may be established in a calibration process, and the relevant relationship, perhaps represented by a table of values, stored in memory of the engine management system 40 for use by the controller 42, as explained further below.

The temperature of the oxygen sensor 30 may be determined based on the resistance of the heater portion 34. For example, the current $I_H$ in the heater portion 34 may be calculated as the voltage drop $V_{HS}$ across the shunt resistor $R_{HS}$, divided by the resistance of the shunt resistor $R_{HS}$, or $I_H=V_{HS}/R_{HS}$. Then, the resistance $R_H$ of the heater portion 34 may be calculated based on the voltage drop across the heater portion 34 divided by the current $I_H$ through the heater portion 34. Thus, $R_H$ may be calculated as $R_H=(12-V_{HS})/I_H$. Then, using $R_H$, temperature T may be calculated using a suitable formula, for example $T=(M \times R_H)+B$, where the slope M and the constant B are dependent on the heater design. As can be appreciated, M and B can be determined in a calibration process, and the relevant values stored in memory of the engine management system 40 for use by the controller 42.

Figure 4:
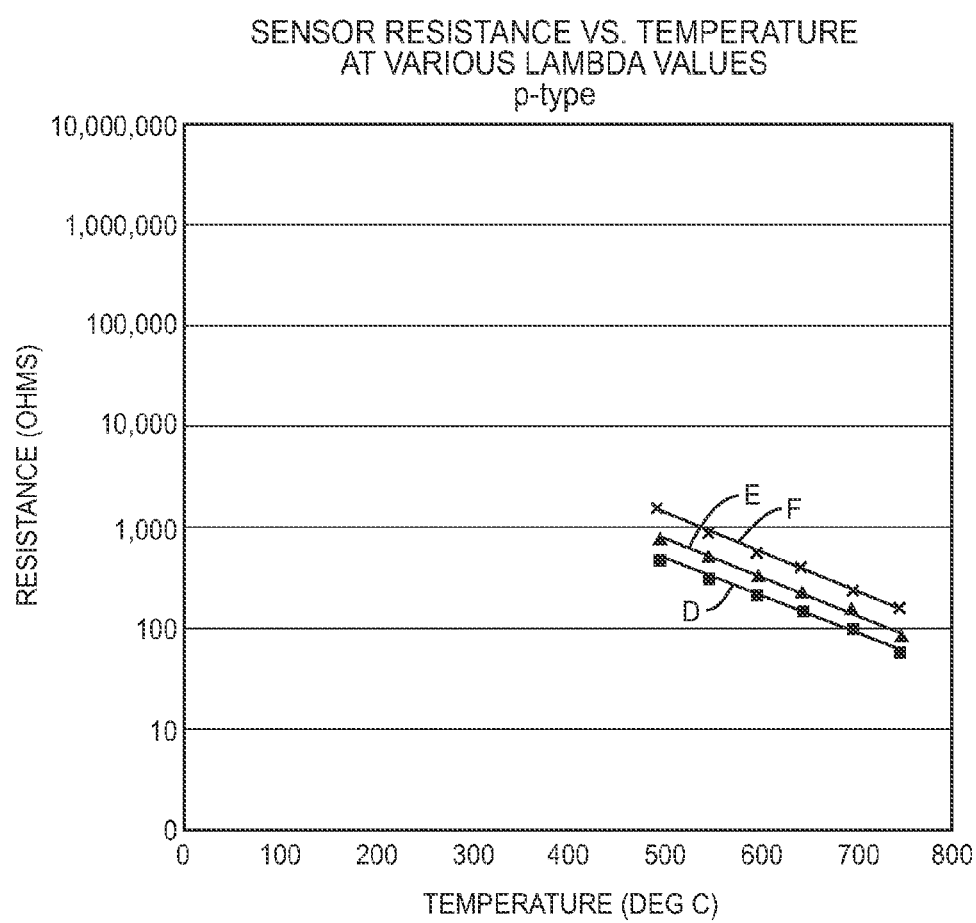
FIG. 4 shows a simplified graphic representation of temperature dependence on resistance of an p-type semiconductor based oxygen sensing circuit, at various $\lambda$ values.

The discussion above has generally been in the context of the oxygen sensor having an n-type semiconductor based oxygen sensing portion 32. However, the oxygen sensing circuit may alternatively be p-type semiconductor based because a p-type semiconductor likewise has a similar response in the lean region. As shown in FIG. 4, a plot of resistance of the oxygen sensing portion 32 versus sensor temperature appears to have a linear decreasing relationship with increasing temperature when plotted on a log scale, as shown by curves D, E, F (which represent various λ values, such as 1.15, 1.10, 1.05, respectively). Thus, the n-type oxygen sensor 30 may be used when the primary concern is sensing oxygen values in the rich region, while the p-type oxygen sensor 30 may be used when the primary concern is sensing oxygen values in the lean region. Of course, the engine 10 may have both an n-type and a p-type oxygen sensor if desired, with the controller 42 using the data from the appropriate sensing circuit 32 for the region for control therein.

The controller 42 receives the inputs from the oxygen sensor 30 and other sensors, and controls the operation of the fuel metering, ignition timing, and other engine functions. Relevant to the present discussion and with reference to FIG. 5, the controller 42 receives sensed oxygen level signal(s) from the resistor network 36, based on signals from the sensing circuit 32 (step 210), and receives sensed temperature signal(s) from the resistor network 36 based on signals from the heater portion 34 (step 220). Based on the sensed oxygen level signal(s), the controller 42 determines a first value indicative of the oxygen level of the exhaust gases (step 215). Further, the controller 42 determines a second value indicative of the temperature of the oxygen sensor based on the sensed temperature signal(s) (step 225). Note that the second value corresponds to the first value so that the determined temperature is the temperature of the oxygen sensor 30 at substantially the same time as the information for the first value is gathered. The controller 42 then determines a third value indicative of the air:fuel ratio as a function of the first and second values (step 230). As can be appreciated, the third value is typically a λ value. The determination of the third value may utilize a look-up table of resistance values, temperature values, and corresponding third values (e.g., λ values), for the particular oxygen sensor, or the "class" of oxygen sensor (e.g., n-type or p-type of a particular model or series). Alternatively, the third value may be determined based on a formula, where both the first and second values are independent variables of the formula. Once the third value is determined, the controller 42 may then control the engine 10 based on the third value, in any suitable fashion (step 240). For example, the controller 42 may cause the fuel metering rate to be increased (lowering λ) or decreased (raising λ), via suitable control signals sent to throttle body and fuel injector 16. As can be appreciated, the controller 42 may repeat the process above by updating the first value, updating the second value, and determining an updated third value based thereon. This updating may occur periodically, or may be a triggered update (such as in response to a change in input air conditions), as is appropriate.

Note that the third value indicative of the air:fuel ratio is a function of both the first value indicative of the oxygen level of the exhaust gases and the second value indicative of the temperature of the oxygen sensor. Thus, the magnitude of the third value varies in dependence on both the first and second values.

The discussion above has generally been in the context of the temperature of the oxygen sensor 30 being derived from the resistance of the heater portion 34 that is part of the oxygen sensor. Thus, the heater portion 34 fills two roles: heating the oxygen sensor and sensing temperature thereof. However, in some embodiments, a temperature sensor distinct from the heater portion 34 may alternatively employed. Thus, the oxygen sensor 30 may include a thermocouple or other suitable temperature sensing device, in addition to the oxygen sensing portion 32 and the heater portion 34. Such a temperature sensor is shown at 35 in FIG. 2 in dashed lines to indicate its optional presence. Note that heater portion 34 is optional, and not required in all embodiments.

Figure 5:
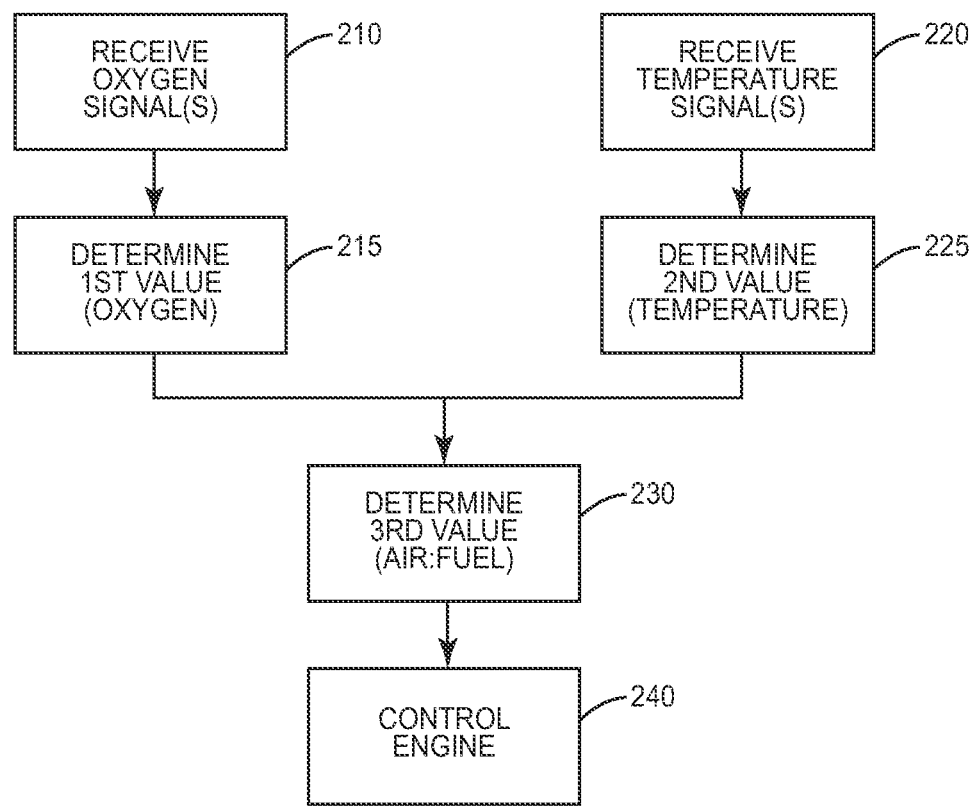
FIG. 5 shows a flowchart of the process of one embodiment of the present invention.
Figure 6:
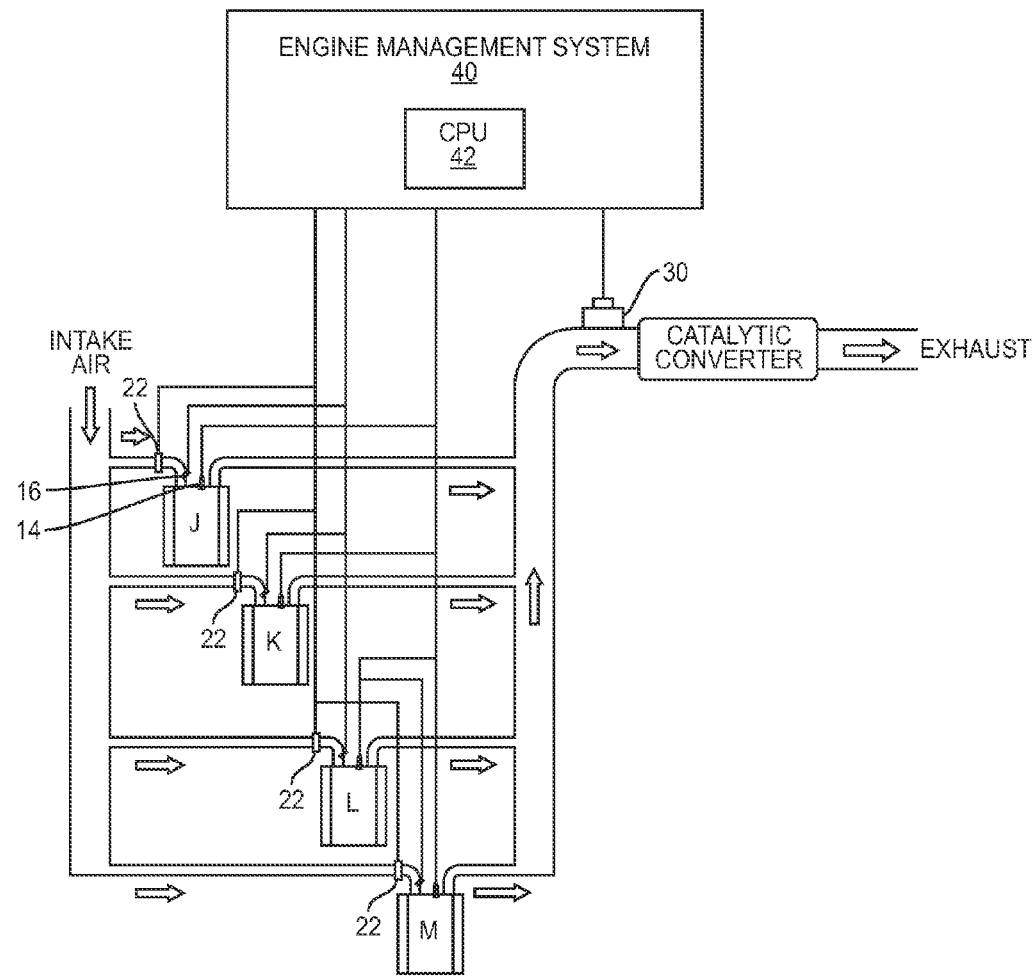
FIG. 6 shows one multiple-cylinder configuration with a common oxygen sensor for all cylinders.
Figure 7:
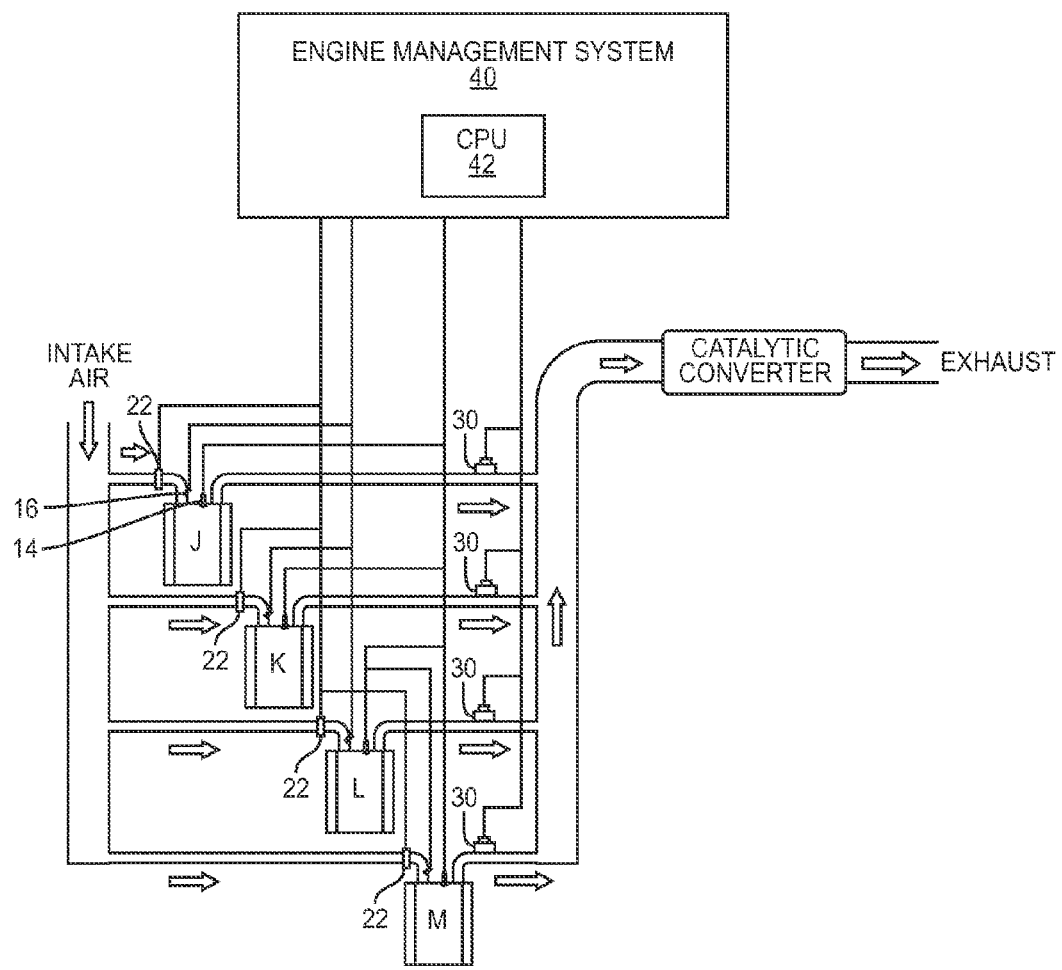
FIG. 7 shows another multiple-cylinder configuration with individual oxygen sensors for each cylinder.

The discussion above has generally been in the context of controlling an engine 10 having a single cylinder/combustion chamber. However, a similar approach may be used with engines having multiple cylinders, such as that shown in FIG. 4 with cylinders J, K, L, and M. In FIG. 4, a single common oxygen sensor 30 is used for multiple cylinders. The controller 42 may control the engine parameters (e.g., fuel metering rate) based on readings from the oxygen sensor 30, or, if the oxygen sensor 30 has fast enough response time, the controller 42 may be able to control the engine parameters on an individual cylinder basis. Another multi-cylinder arrangement is shown in FIG. 5, where each cylinder has its own dedicated oxygen sensor 30. With this arrangement, the controller 42 may more easily control the cylinder-specific engine parameters (e.g., fuel metering rate) on an individual cylinder basis based on readings from the corresponding oxygen sensor 30.

The discussion above has generally been in the context of an internal combustion engine; however, the present invention is not limited in application to internal combustion engines. Indeed, the oxygen sensing method described above can be used to control combustion processes generally. Thus, for example, the method(s) described herein may be used in combustion processes in a furnace or a water heater. As with the engine-based discussion above, the oxygen sensor 30 is disposed so as to sense exhaust gases in the exhaust plenum 19 from the combustion process.

The methods and engine control systems discussed above provide the opportunity for enhanced combustion and/or engine control so that greater fuel economy and/or reduced emissions may be achieved.

As used herein, an air:fuel ratio may be expressed as an un-normalized ratio (e.g., 14.7:1 for gasoline), or as a normalized ratio (e.g., $\lambda$).

The disclosure of all patents and patent publications mentioned above are incorporated herein by reference in their entirety.

The present invention may, of course, be carried out in other specific ways than those herein set forth without departing from the scope of the invention. The present embodiments are, therefore, to be considered as illustrative and not restrictive.

What is claimed is:

1. A method of determining an air:fuel ratio of a combustion process, based on information from an oxygen sensor exposed to exhaust gas from the combustion process, the method comprising:
    determining a first value indicative of oxygen content of the exhaust gas based on information from an oxygen sensing portion of the oxygen sensor;
    determining a second value indicative of a temperature of the oxygen sensor corresponding in time to the first value;
    determining a third value indicative of the air:fuel ratio as a function of the first and second values, wherein the third value varies in dependence on both the first value and the second value.

2. The method of claim 1 wherein determining the first value comprises measuring a voltage drop of a circuit comprising the oxygen sensing portion.

3. The method of claim 1:
    wherein the oxygen sensor has an electric resistance heater portion;
    wherein the determining the second value comprises determining the second value based on a resistance of the heater portion.

4. The method of claim 3, wherein determining the second value comprises measuring a voltage drop of a circuit comprising the heater portion.

5. The method of claim 1, further comprising, thereafter controlling operation of the combustion process based on the third value.

6. The method of claim 5, wherein the controlling operation of the combustion process comprises adjusting a fuel metering rate based on the third value.

7. The method of claim 1, wherein the oxygen sensing portion comprises an n-type semiconductor.

8. The method of claim 1, wherein the oxygen sensing portion comprises a p-type semiconductor.

9. The method of claim 1, wherein determining the third value comprises referencing a look-up table containing predetermined values of corresponding to the first value and the second value.

10. The method of claim 1, wherein the determining the third value comprises calculating the third value according to a formula, wherein the formula has the first and second values as independent variables.

11. The method of claim 1, wherein the combustion process occurs in an internal combustion engine.

12. The method of claim 11, wherein the engine is a multi-cylinder engine, and wherein the oxygen sensor is associated with only one cylinder of the engine.

13. The method of claim 11, wherein the engine is a multi-cylinder engine, and wherein the oxygen sensor is associated with a plurality of cylinders of the engine.

14. The method of claim 1:
    wherein the determining the first value comprises determining a resistance of the oxygen sensing portion;
    wherein the determining the resistance of the oxygen sensing portion comprises determining a voltage drop across a shunt resistor disposed in series with the oxygen sensing portion.

15. The method of claim 1, wherein determining the second value comprises determining the second value based on a temperature sensor of the oxygen sensor, but distinct from a heater portion of the oxygen sensor.

16. An oxygen sensing apparatus, comprising:
    an oxygen sensor disposed so as to be exposed to exhaust gas from the combustion process; the oxygen sensor having an oxygen sensing portion;
    one or more processing circuits operatively connected to the oxygen sensor and configured to:
        determine a first value indicative of oxygen content of the exhaust gas based on information from the oxygen sensing portion of the oxygen sensor;
        determine a second value indicative of a temperature of the oxygen sensor corresponding in time to the first value;

determine a third value indicative of the air:fuel ratio as a function of the first and second values, wherein the third value varies in dependence on both the first value and the second value.

17. The oxygen sensing apparatus of claim 16:
wherein the oxygen sensor further comprises a heater portion;
wherein the one or more processing circuits are configured to determine the second value based on a resistance of the heater portion.

18. The oxygen sensing apparatus of claim 16, wherein the one or more processing circuits are further configured to control the combustion process based on the third value.

19. The oxygen sensing apparatus of claim 16, wherein the oxygen sensing apparatus is a portion of an internal combustion engine.

20. The oxygen sensing apparatus of claim 16:
wherein the combustion process in a combustion chamber of an internal combustion engine;
wherein the one or more processing circuits are further configured to thereafter control operation of the engine based on the third value.

* * * * *